(12) United States Patent
Hatib et al.

(10) Patent No.: US 8,905,939 B2
(45) Date of Patent: Dec. 9, 2014

(54) METHOD AND APPARATUS FOR CONTINUOUS ASSESSMENT OF A CARDIOVASCULAR PARAMETER USING THE ARTERIAL PULSE PRESSURE PROPAGATION TIME AND WAVEFORM

(75) Inventors: Feras S. Hatib, Irvine, CA (US); Charles R. Mooney, Costa Mesa, CA (US); Luchy D. Roteliuk, Lake Forest, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1562 days.

(21) Appl. No.: 11/593,247

(22) Filed: Nov. 6, 2006

(65) Prior Publication Data
US 2008/0033305 A1    Feb. 7, 2008

Related U.S. Application Data

(60) Provisional application No. 60/830,735, filed on Jul. 13, 2006.

(51) Int. Cl.
| | |
|---|---|
| *A61B 5/02* | (2006.01) |
| *A61B 5/0285* | (2006.01) |
| *A61B 5/029* | (2006.01) |
| *A61B 5/0402* | (2006.01) |
| *A61B 5/021* | (2006.01) |
| *A61B 5/053* | (2006.01) |

(52) U.S. Cl.
CPC .............. *A61B 5/0285* (2013.01); *A61B 5/0535* (2013.01); *A61B 5/029* (2013.01); *A61B 5/0402* (2013.01); *A61B 5/021* (2013.01)
USPC .......................................... 600/485; 600/481

(58) Field of Classification Search
USPC .................................................. 600/481–528
See application file for complete search history.

(56) References Cited

U.S. PATENT DOCUMENTS

| | | |
|---|---|---|
| 4,236,527 A | 12/1980 | Newbower et al. |
| 4,507,974 A | 4/1985 | Yelderman |
| 5,146,414 A | 9/1992 | McKown et al. |

(Continued)

FOREIGN PATENT DOCUMENTS

| | | | | |
|---|---|---|---|---|
| WO | WO-00/47110 | | 8/2000 | |
| WO | WO 00/47110 | * | 8/2000 | ........... A61B 5/0225 |
| WO | 2005055825 A1 | | 6/2005 | |

OTHER PUBLICATIONS

Juan Du; Gangmin Ning; Yingqi Li; Xiaoxiang Zheng; , "Arterial Stiffness Estimation in Hypertension," Engineering in Medicine and Biology Society, 2005. IEEE-EMBS 2005. 27th Annual International Conference of the , vol., No., pp. 5507-5510, Jan. 17-18, 2006 doi: 10.1109/IEMBS.2005.1615730.*

(Continued)

*Primary Examiner* — Michael Kahelin
*Assistant Examiner* — Karen Toth
(74) *Attorney, Agent, or Firm* — Michael Crapenhoft

(57) ABSTRACT

A method and apparatus for determining a cardiovascular parameter including receiving an input signal corresponding to an arterial blood pressure measurement over an interval that covers at least one cardiac cycle, determining a propagation time of the input signal, determining at least one statistical moment of the input signal, and determining an estimate of the cardiovascular parameter using the propagation time and the at least one statistical moment.

15 Claims, 12 Drawing Sheets

(56) References Cited

U.S. PATENT DOCUMENTS

| | | | |
|---|---|---|---|
| 5,199,438 A * | 4/1993 | Pearlman | 600/483 |
| 5,309,916 A * | 5/1994 | Hatschek | 600/485 |
| 5,400,793 A | 3/1995 | Wesseling | |
| 5,535,753 A | 7/1996 | Petrucelli et al. | |
| 5,687,733 A | 11/1997 | McKown | |
| 6,071,244 A | 6/2000 | Band et al. | |
| 6,315,735 B1 | 11/2001 | Joeken et al. | |
| 6,348,038 B1 | 2/2002 | Band et al. | |
| 6,354,999 B1 | 3/2002 | Dgany et al. | |
| 6,371,923 B1 | 4/2002 | Roteliuk et al. | |
| 6,485,431 B1 * | 11/2002 | Campbell | 600/526 |
| 6,647,287 B1 * | 11/2003 | Peel et al. | 600/513 |
| 6,652,466 B2 | 11/2003 | Sugo et al. | |
| 6,676,608 B1 | 1/2004 | Keren | |
| 6,758,822 B2 | 7/2004 | Ramano | |
| 2003/0167012 A1 * | 9/2003 | Friedman et al. | 600/506 |
| 2004/0015091 A1 * | 1/2004 | Greenwald et al. | 600/513 |
| 2005/0124903 A1 * | 6/2005 | Roteliuk et al. | 600/526 |
| 2005/0124904 A1 * | 6/2005 | Roteliuk | 600/526 |
| 2005/0222514 A1 | 10/2005 | Sugo et al. | |
| 2007/0276632 A1 * | 11/2007 | Banet et al. | 702/187 |
| 2008/0015451 A1 | 1/2008 | Hatib | |

OTHER PUBLICATIONS

Age-related factors that confound peripheral pulse timing characteristics in Caucasian children Jya Foo, SJ Wilson, G Williams, M-A Harris and D Cooper, Journal of Human Hypertension (2005) 19, 463-466. doi:10.1038/sj.jhh.1001846 Published online Feb. 24, 2005.*

"The Static Elastic Properties of 45 Human Thoracic and 20 Abdominal Aortas in vitro and the Parameters of a New Model," J. Biomechanics, vol. 17, No. 6, pp. 425-435, 1984.

"Ueber die Messung des Schlagvolumens des Herzens auf unblutigem Wegf," Zeitung fur Biologie 90 (1930) 467-507.

Kontis S., et al. On-line Doppler ultrasound measurement of aortic compliance and its repeatability in normal subjects, Clinical Physics and Physiological Measurement, Institute of Physics Publishing, Bristol, GB, vol. 10, No. 2, May 1, 1989 pp. 127-135, XP020025997 ISSN: 0143-0815 See section 3.1.

International Search Report for Patent Application No. PCT/US2007/073216, Filed Jul. 11, 2007.

Australian Office Action, May 17, 2012.

European Office Action, Feb. 13, 2012.

Japanese Office Action, Nov. 2, 2012.

* cited by examiner

METHOD AND APPARATUS FOR CONTINUOUS ASSESSMENT OF A CARDIOVASCULAR PARAMETER USING THE ARTERIAL PULSE PRESSURE PROPAGATION TIME AND WAVEFORM

CLAIM OF PRIORITY UNDER 35 U.S.C. §119

The present application for patent claims priority to Provisional Application No. 60/830,735 entitled "METHOD AND APPARATUS FOR CONTINUOUS ASSESSMENT OF A CARDIOVASCULAR PARAMETER USING THE ARTERIAL PULSE PRESSURE PROPAGATION TIME AND WAVEFORM," filed Jul. 13, 2006, and assigned to the assignee hereof and hereby expressly incorporated by reference herein.

FIELD OF THE INVENTION

The invention relates generally to a system and method for hemodynamic monitoring. More particularly, the invention relates to a system and method for estimation of at least one cardiovascular parameter, such as vascular tone, arterial compliance or resistance, stroke volume (SV), cardiac output (CO), etc., of an individual using a measurement of an arterial pulse pressure propagation time and a waveform.

DESCRIPTION OF THE RELATED ART

Cardiac output (CO) is an important indicator not only for diagnosis of disease, but also for continuous monitoring of the condition of both human and animal subjects, including patients. Few hospitals are therefore without some form of conventional equipment to monitor cardiac output.

One way to measure CO is using the well-known formula:

$$CO = HR * SV, \quad \text{(Equation 1)}$$

where SV represents the stroke volume and HR represents the heart rate. The SV is typically measured in liters and the HR is typically measured in beats per minute, although other units of volume and time may be used. Equation 1 expresses that the amount of blood the heart pumps out over a unit of time (such as a minute) is equal to the amount it pumps out on every beat (stroke) times the number of beats per time unit.

Since the HR is easy to measure using a wide variety of instruments, the calculation of CO usually depends on some technique for estimating the SV. Conversely, any method that directly yields a value for CO can be used to determine the SV by dividing by the HR. Estimates of CO or SV can then be used to estimate, or contribute to estimating, any parameter that can be derived from either of these values.

One invasive method to determine CO (or equivalently SV) is to mount a flow-measuring device on a catheter, and then to thread the catheter into the subject and to maneuver it so that the device is in or near the subject's heart. Some such flow-measuring devices inject either a bolus of material or energy (usually heat) at an upstream position, such as in the right atrium, and determine flow based on the characteristics of the injected material or energy at a downstream position, such as in the pulmonary artery. Patents that disclose implementations of such invasive techniques (in particular, thermodilution) include:

U.S. Pat. No. 4,236,527 (Newbower et al., 2 Dec. 1980);
U.S. Pat. No. 4,507,974 (Yelderman, 2 Apr. 1985);
U.S. Pat. No. 5,146,414 (McKown et al., 8 Sep. 1992); and
U.S. Pat. No. 5,687,733 (McKown et al., 18 Nov. 1997).

Still other invasive devices are based on the known Fick technique, according to which CO is calculated as a function of oxygenation of arterial and mixed venous blood. In most cases, oxygenation is sensed using right-heart catheterization. There have, however, also been proposals for systems that non-invasively measure arterial and venous oxygenation, in particular, using multiple wavelengths of light; but to date they have not been accurate enough to allow for satisfactory CO measurements on actual patients.

Invasive methods have obvious disadvantages. One such disadvantage is that the catheterization of the heart is potentially dangerous, especially considering that the subjects (especially intensive care patients) on which it is performed are often already in the hospital because of some actually or potentially serious condition. Invasive methods also have less obvious disadvantages. One such disadvantage is that thermo-dilution relies on assumptions such as uniform dispersion of the injected heat that affects the accuracy of the measurements depending on how well they are fulfilled. Moreover, the introduction of an instrument into the blood flow may affect the value (for example, flow rate) that the instrument measures. Therefore, there has been a long-standing need for a method of determining CO that is both non-invasive (or at least as minimally invasive as possible) and accurate.

One blood characteristic that has proven particularly promising for accurately determining CO less invasively or non-invasively is blood pressure. Most known blood pressure based systems rely on the pulse contour method (PCM), which calculates an estimate of CO from characteristics of the beat-to-beat arterial pressure waveform. In the PCM, "Windkessel" (German for "air chamber") parameters (characteristic impedance of the aorta, compliance, and total peripheral resistance) are used to construct a linear or non-linear hemodynamic model of the aorta. In essence, blood flow is analogized to a flow of electrical current in a circuit in which an impedance is in series with a parallel-connected resistance and capacitance (compliance).

The three required parameters of the model are usually determined either empirically, through a complex calibration process, or from compiled "anthropometric" data, that is, data about the age, sex, height, weight, etc., of other patients or test subjects. U.S. Pat. No. 5,400,793 (Wesseling, 28 Mar. 1995) and U.S. Pat. No. 5,535,753 (Petrucelli et al., 16 Jul. 1996) are representative of systems that utilize a Windkessel circuit model to determine CO.

Many extensions to the simple two-element Windkessel model have been proposed in hopes of better accuracy. One such extension was developed by the Swiss physiologists Broemser and Ranke in their 1930 article "Ueber die Messung des Schlagvolumens des Herzens auf unblutigem Wegf," Zeitung für Biologie 90 (1930) 467-507. In essence, the Broemser model—also known as a three-element Windkessel model—adds a third element to the basic two-element Windkessel model to simulate resistance to blood flow due to the aortic or pulmonary valve.

PCM systems can monitor CO more or less continuously, without the need for a catheter to be left in the patient. Indeed, some PCM systems operate using blood pressure measurements taken using a finger cuff. One drawback of PCM systems, however, is that they are no more accurate than the rather simple, three-parameter model from which they are derived; in general, a model of a much higher order would be needed to accurately account for other phenomena, such as the complex pattern of pressure wave reflections due to multiple impedance mis-matches caused by, for example, arterial branching. Other improvements have therefore been proposed, with varying degrees of complexity.

The "Method and Apparatus for Measuring Cardiac Output" disclosed by Salvatore Romano in U.S. Pat. No. 6,758,822, for example, represents a different attempt to improve upon PCM methods by estimating the SV, either invasively or non-invasively, as a function of the ratio between the area under the entire pressure curve and a linear combination of various components of impedance. In attempting to account for pressure reflections, the Romano system relies not only on accurate estimates of inherently noisy derivatives of the pressure function, but also on a series of empirically determined, numerical adjustments to a mean pressure value.

At the core of several methods for estimating CO is an expression of the form:

$$CO = HR*(K*SV_{est}) \quad \text{(Equation 2)}$$

where HR is the heart rate, $SV_{est}$ is the estimated stroke volume, and K is a scaling factor related to arterial compliance. Romano and Petrucelli, for example, rely on this expression, as do the apparatuses disclosed in U.S. Pat. No. 6,071,244 (Band et al., 6 Jun. 2000) and U.S. Pat. No. 6,348,038 (Band et al., 19 Feb. 2002).

Another expression often used to determines CO is:

$$CO = MAP*C/tau \quad \text{(Equation 3)}$$

where MAP is mean arterial pressure, tau is an exponential pressure decay constant, and C, like K, is a scaling factor related to arterial compliance K. U.S. Pat. No. 6,485,431 (Campbell, 26 Nov. 2002) discloses an apparatus that uses such an expression.

The accuracy of these methods may depend on how the scaling factors K and C are determined. In other words, an accurate estimate of compliance (or of some other value functionally related to compliance) may be required. For example, Langwouters ("The Static Elastic Properties of 45 Human Thoracic and 20 Abdominal Aortas in vitro and the Parameters of a New Model," J. Biomechanics, Vol. 17, No. 6, pp. 425-435, 1984) discusses the measurement of vascular compliance per unit length in human aortas and relates it to a patient's age and sex. An aortic length is determined to be proportional to a patient's weight and height. A nomogram, based on this patient information, is then derived and used in conjunction with information derived from an arterial pressure waveform to improve an estimate of the compliance factor.

It is likely that the different prior art apparatuses identified above, each suffer from one or more drawbacks. The Band apparatus, for example, requires an external calibration using an independent measure of CO to determine a vascular impedance-related factor that is then used in CO calculations. U.S. Pat. No. 6,315,735 (Joeken et al., 13 Nov. 2001) describes another device with the same shortcoming.

Wesseling (U.S. Pat. No. 5,400,793, 28 Mar. 1995) attempts to determine a vascular compliance-related factor from anthropometric data such as a patient's height, weight, sex, age, etc. This method relies on a relationship that is determined from human nominal measurements and may not apply robustly to a wide range of patients.

Romano attempts to determine a vascular impedance-related factor solely from features of the arterial pressure waveform, and thus fails to take advantage of known relationships between patient characteristics and compliance. In other words, by freeing his system of a need for anthropometric data, Romano also loses the information contained in such data. Moreover, Romano bases several intermediate calculations on values of the derivatives of the pressure waveform. As is well known, however, such estimates of derivatives are inherently noisy. Romano's method has, consequently, been unreliable.

What is needed is a system and method for more accurately and robustly estimating cardiovascular parameters such as arterial compliance (K or C) or resistance, vascular tone, tau, or values computed from these parameters, such as the SV and the CO.

One of the present inventors earlier published that the SV can be approximated as being proportional to the standard deviation of the arterial pressure waveform P(t), or of some other signal that itself is proportional to P(t): U.S. Published Patent Application No. 2005/0124903 A1 (Luchy Roteliuk et al., 9 Jun. 2005, "Pressure based System and Method for Determining Cardiac Stroke Volume"). Thus, one way to estimate the SV is to apply the relationship:

$$SV = K\sigma(P) = Kstd(P) \quad \text{(Equation 4)}$$

where K is a scaling factor and from which follows:

$$CO = K\sigma(P)HR = Kstd(P)HR \quad \text{(Equation 5)}$$

This proportionality between the SV and the standard deviation of the arterial pressure waveform is based on the observation that the pulsatility of a pressure waveform is created by the cardiac SV into the arterial tree as a function of the vascular tone (i.e., vascular compliance and peripheral resistance). The scaling factor K of equations 4 and 5 is an estimate of the vascular tone.

Recently, one of the present inventors also published that vascular tone can be reliably estimated using the shape characteristics of the arterial pulse pressure waveform in combination with a measure of the pressure dependant vascular compliance and the patient's anthropometric data such as age, gender, height, weight and body surface area (BSA): U.S. Published Patent No. 2005/0124904 A1 (Luchy Roteliuk, 9 Jun. 2005, "Arterial pressure-based automatic determination of a cardiovascular parameter"). To quantify the shape information of the arterial pulse pressure waveform, he used higher order time domain statistical moments of the arterial pulse pressure waveform (such as kurtosis and skewness) in addition to the newly derived pressure weighted statistical moments. Thus, the vascular tone is computed as a function of a combination of parameters using a multivariate regression model with the following general form:

$$K = \chi(\mu_{T1}, \mu_{T2}, \ldots \mu_{Tk}, \mu_{P1}, \mu_{P2}, \ldots \mu_{Pk}, C(P), BSA, Age, G \ldots) \quad \text{(Equation 6)}$$

where
K is vascular tone (the calibration factor in equations 4 and 5);
X is a multiregression statistical model;
$\mu_{1T} \ldots \mu_{kT}$ are the 1-st to k-th order time domain statistical moments of the arterial pulse pressure waveform;
$\mu_{1P} \ldots \mu_{kP}$ are the 1-st to k-th order pressure weighted statistical moments of the arterial pulse pressure waveform;
C(P) is a pressure dependent vascular compliance computed using methods proposed by Langwouters et al 1984 ("The Static Elastic Properties of 45 Human Thoracic and 20 Abdominal Aortas in vitro and the Parameters of a New Model," J. Biomechanics, Vol. 17, No. 6, pp. 425-435, 1984);
BSA is a patient's body surface area (function of height and weight);
Age is a patient's age; and
G is a patient's gender.

The predictor variables set for computing the vascular tone factor K, using the multivariate model χ, were related to the "true" vascular tone measurement, determined as a function of CO measured through thermo-dilution and the arterial pulse pressure, for a population of test or reference subjects. This creates a suite of vascular tone measurements, each of which is a function of the component parameters of χ. The multivariate approximating function is then computed, using known numerical methods, that best relates the parameters of χ to a given suite of CO measurements in some predefined sense. A polynomial multivariate fitting function is used to generate the coefficients of the polynomial that gives a value of χ for each set of the predictor variables. Thus, the multivariate model has the following general form:

$$\chi = [A_1 \quad A_2 \quad \cdots \quad A_n] * \begin{bmatrix} X_1 \\ X_2 \\ \cdots \\ X_n \end{bmatrix} \quad \text{(Equation 7)}$$

$$\chi = [A_1 \quad A_2 \quad \cdots \quad A_n] * \begin{bmatrix} X_1 \\ X_2 \\ \cdots \\ X_n \end{bmatrix}$$

where $A_1 \ldots A_n$ are the coefficients of the polynomial multi-regression model, and X are the model's predictor variables:

$$X_{n,1} = \quad \text{(Equation 8)}$$

$$\prod_m \left( \begin{bmatrix} \mu_{T1} \cdots \mu_{Tk} & \mu_{P1} \cdots \mu_{P1} \cdots \\ \mu_{Tk} C(P) & BSA & Age & G & \cdots \end{bmatrix} \wedge \begin{bmatrix} P_{1,1} & \cdots & P_{1,m} \\ \cdots & \cdots & \cdots \\ P_{n,1} & \cdots & P_{n,m} \end{bmatrix} \right)$$

The method listed above relies solely on a single arterial pulse pressure measurement. Its simplicity and the fact that it does not require a calibration are advantages of this method. However, due to the empirical nature of the vascular tone assessment relationships, the accuracy of this method may be low in some extreme clinical situations where the basic empirical relationships of the model are not valid. For this reason, a second independent measurement may be beneficial if added to the basic multiregression model.

As shown above, many techniques have been devised, both non-invasive and invasive, for measuring the SV and CO, and particularly for detecting vascular compliance, peripheral resistance and vascular tone. It should be appreciated that there is a need for a system and method for estimating CO, or any parameter that can be derived from or using CO, that is robust and accurate and that is less sensitive to calibration and computational errors.

SUMMARY OF THE INVENTION

One embodiment of the invention provides a method for determining a cardiovascular parameter including receiving an input signal corresponding to an arterial blood pressure measurement over an interval that covers at least one cardiac cycle, determining a propagation time of the input signal, determining at least one statistical moment of the input signal, and determining an estimate of the cardiovascular parameter using the propagation time and the at least one statistical moment.

One embodiment of the invention provides an apparatus for determining a cardiovascular parameter including a processing unit to receive an input signal corresponding to an arterial blood pressure measurement over an interval that covers at least one cardiac cycle, determine a propagation time of the input signal, determine at least one statistical moment of the input signal and determine an estimate of the cardiovascular parameter using the propagation time and the at least one statistical moment.

DETAILED DESCRIPTION

Methods and systems that implement the embodiments of the various features of the invention will now be described with reference to the drawings. The drawings and the associated descriptions are provided to illustrate embodiments of the invention and not to limit the scope of the invention. Reference in the specification to "one embodiment" or "an embodiment" is intended to indicate that a particular feature, structure, or characteristic described in connection with the embodiment is included in at least an embodiment of the invention. The appearances of the phrase "one embodiment" or "an embodiment" in various places in the specification are not necessarily all referring to the same embodiment. Throughout the drawings, reference numbers are re-used to indicate correspondence between referenced elements.

In broadest terms, the invention involves the determination of a cardiac value, such as a stroke volume (SV), and/or a value derived from the SV such as cardiac output (CO), using the arterial pulse pressure propagation time. The arterial pulse pressure propagation time may be measured by using arterial pressure waveforms or waveforms that are proportional to or derived from the arterial pulse pressure, electrocardiogram measurements, bioimpedance measurements, other cardiovascular parameters, etc. These measurements may be made with an invasive, non-invasive or minimally invasive instrument or a combination of instruments.

The invention may be used with any type of subject, whether human or animal. Because it is anticipated that the most common use of the invention will be on humans in a diagnostic setting, the invention is described below primarily in use with a "patient." This is by way of example only; however, it is intended that the term "patient" should encompass all subjects, both human and animal, regardless of setting.

Figure 1:
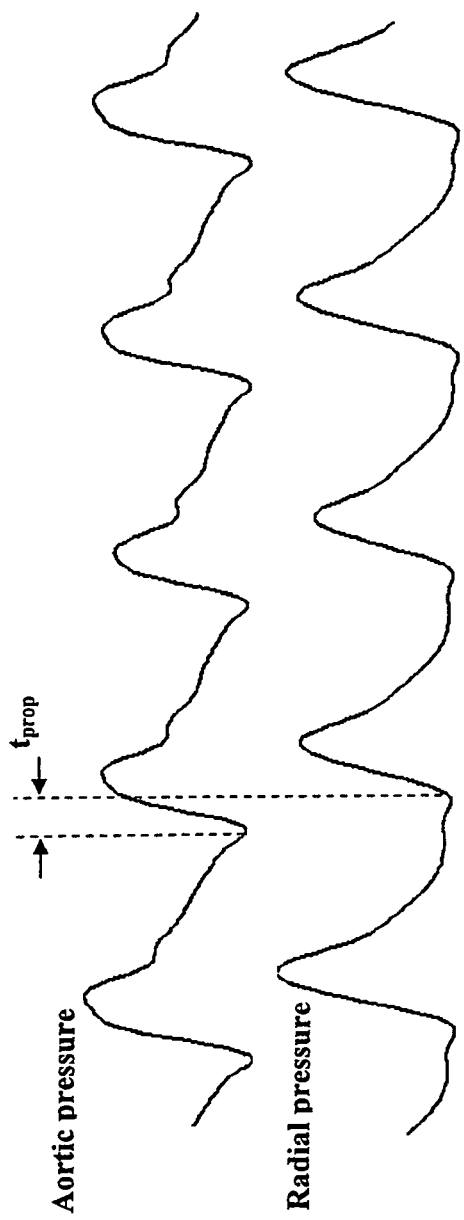
FIG. 1 illustrates an example of two blood pressure curves representing two different arterial pressure measurements received from a subject according to an embodiment of the invention.

FIG. 1 illustrates an example of two blood pressure curves representing two different arterial pressure measurements received from a subject. The top curve represents a central arterial pressure measurement detected from the subject's aorta and the bottom curve represents a measurement detected from the subject's radial artery. The pulse pressure propagation time ($t_{prop}$) can be measured as the transit time between the two arterial pressure measurements.

The rationale of using the pulse pressure propagation time for hemodynamic measurements is based on a basic principle of cardiovascular biomechanics. That is, if the subject's heart pumped blood through a completely rigid vessel, upon contraction of the heart, the pressure waveform would instantaneously be present at any distal arterial location in the subject's body. However, if the subject's heart pumped blood through a compliant vessel, upon contraction of the heart, the pressure waveform would be present some amount of time after the heart contracted at a distal arterial location in the subject's body.

The pulse pressure propagation time can be measured invasively or non-invasively at several different locations on the pressure waveform (or any other waveform related to the pressure waveform). In the example shown on FIG. 1, the pulse pressure propagation time may be measured by using two different arterial pressure measurements, for example, one reference measurement from the aorta and one peripheral measurement from the radial artery.

Figure 2:
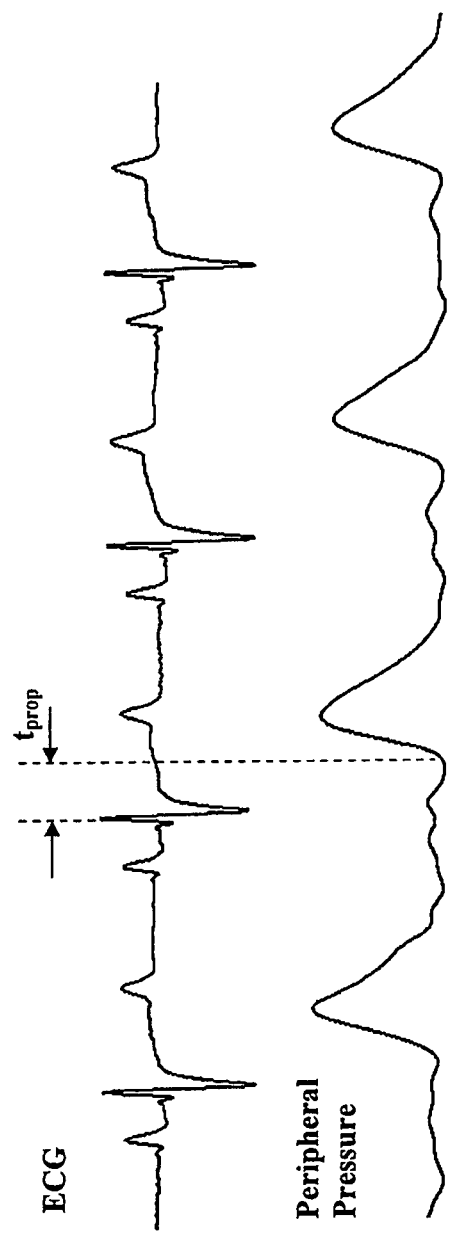
FIG. 2 illustrates an example of an Electrocardiogram measurement (ECG) and a blood pressure measurement received from a subject according to an embodiment of the invention.

FIG. 2 illustrates an example of using an electrocardiogram signal as a reference signal for the propagation time measurement. The top curve represents an electrocardiogram (ECG) signal detected with electrodes placed near the subject's heart and the bottom curve represents an arterial pressure measurement detected from the subject's peripheral artery. In this example, the arterial pulse pressure propagation time ($t_{prop}$) may be measured by using the transit time between the ECG signal and the peripheral arterial pressure. Similarly, a transthoracic bioimpedance measurement could be used as a reference site, and the propagation time could be measured as a transit time versus a peripheral measurement derived from or proportional to the arterial blood pressure.

The arterial pulse pressure propagation time provides an indirect measure of the physical (i.e., mechanical) properties of a vessel segment between the two recording sites. These properties include primarily the elastic and geometric properties of the arterial walls. The properties of the arterial walls, for example their thicknesses and lumen diameters, are some of the major determinants of the arterial pulse pressure propagation time. As a result, the pulse pressure propagation time depends mainly on the arterial compliance.

Figure 3:
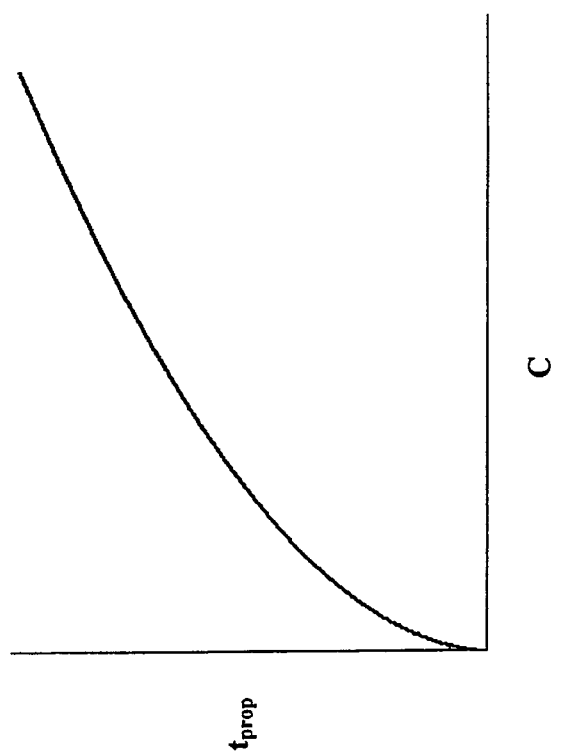
FIG. 3 is a graph illustrating the relationship between the arterial pulse pressure propagation time and the arterial compliance according to an embodiment of the invention.

FIG. 3 illustrates an example where the pulse pressure propagation time increases with increasing arterial compliance (C). Hence, the pulse pressure propagation time ($t_{prop}$) can be represented as a function of arterial compliance (C), i.e., $$t_{prop} = f(C) \qquad \text{(Equation 9)}$$

The arterial pulse pressure propagation time can therefore be used as a simple measure to estimate the arterial compliance. The propagation time can be used as a separate measure to assess a patient's vascular status or can be used in a pulse contour cardiac output algorithm along with other parameters to account for the effects of vascular compliance, vascular resistance and vascular torie. In one embodiment, the arterial pulse pressure propagation time is measured using an arterial pulse pressure signal from relatively large arteries (e.g., radial, femoral, etc.) and therefore the influence of the peripheral resistance is minimal. Also, this measurement may include the average arterial compliance between the measurement sites and may not reflect the pressure dependence of the arterial compliance.

The basic relationship could be derived from the well known Bramwell-Hill equation used to calculate the pulse wave velocity (PWV):

$$PWV^2 = \frac{dP}{dV} \cdot \frac{1}{\rho} \cdot V \qquad \text{(Equation 10)}$$

where
dP is the change in pressure;
dV is the change in volume;
$\rho$ is the blood density; and
V is the baseline volume.

The arterial compliance (C) may be defined as the ratio of the incremental change in volume (dV) resulting from an incremental change in pressure (dP), i.e., $$C = \frac{dV}{dP} \qquad \text{(Equation 11)}$$

Substituting equation (11) into equation (10), we obtain the following equation:

$$PWV^2 = \frac{1}{C} \cdot \frac{1}{\rho} \cdot V \qquad \text{(Equation 12)}$$

On the other hand PWV is defined as follows:

$$PWV = \frac{L}{t_{prop}} \qquad \text{(Equation 13)}$$

where L is the vascular length between the two recording sites and $t_{prop}$ is the arterial pulse pressure propagation time.

If equation 13 is substituted into equation 12, the arterial compliance can be given by:

$$C = \frac{1}{L^2} \cdot \frac{1}{\rho} \cdot V \cdot t_{prop}^2 \qquad \text{(Equation 14)}$$

If we define $\gamma$ as:

$$\gamma = \frac{1}{L^2} \cdot \frac{1}{\rho} \cdot V \qquad \text{(Equation 15)}$$

The arterial compliance can be represented as:

$$C = \gamma \cdot t_{prop}^2 \quad \text{(Equation 16)}$$

where the scaling factor γ is a function, which depends on the blood density, the effective vascular distance between the two recording sites and the basic volume, i.e., γ depends on the physical vascular volume between the two recording site and the blood viscosity (i.e., Hematocrit . . . etc).

Based on the above equations, the arterial pulse pressure propagation time can be used in a number of different ways.

1. The use of the arterial pulse pressure propagation time to estimate arterial compliance. The pulse pressure propagation time may be used as an input to a hemodynamic model based on the standard deviation of the arterial pulse pressure to evaluate the dynamic changes in the arterial pressure created by the systolic ejection. The CO can be represented as a function of the standard deviation of the arterial pulse pressure as follow:

$$CO = K * std(P) * HR \quad \text{(Equation 17)}$$

where K, as we have shown above, is a scaling factor proportional to the arterial compliance, std(P) is the standard deviation of the arterial pulse pressure, and HR is the heart rate.

It is also understood that:

$$CO = C \cdot \frac{MAP}{\tau} \quad \text{(Equation 18)}$$

where MAP is the mean arterial pressure, τ is an exponential pressure decay constant, and C, like K, is a scaling factor related to arterial compliance.

From equations 17 and 18, the scaling factor K is a measure equal to vascular compliance. If we substitute the scaling factor K in equation 17 for the compliance as given in equation 16, CO can be computed using the standard deviation of the arterial pulse pressure waveform and the arterial pulse pressure propagation time:

$$CO = \gamma \cdot t_{prop}^2 \cdot std(P) \cdot HR \quad \text{(Equation 19)}$$

where standard deviation of the arterial pulse pressure can be calculated using the equation:

$$std(P) = \sqrt{\frac{1}{n-1} \sum_{k=1}^{n} [P(k) - P_{avg}]^2} \quad \text{(Equation 20)}$$

where n is the total number of samples, P(k) is the instantaneous pulse pressure, and $P_{avg}$ is the mean arterial pressure. The mean arterial pressure can be defined as:

$$P_{avg} = \frac{1}{n} \sum_{k=1}^{n} P(k) \quad \text{(Equation 21)}$$

Figure 4:
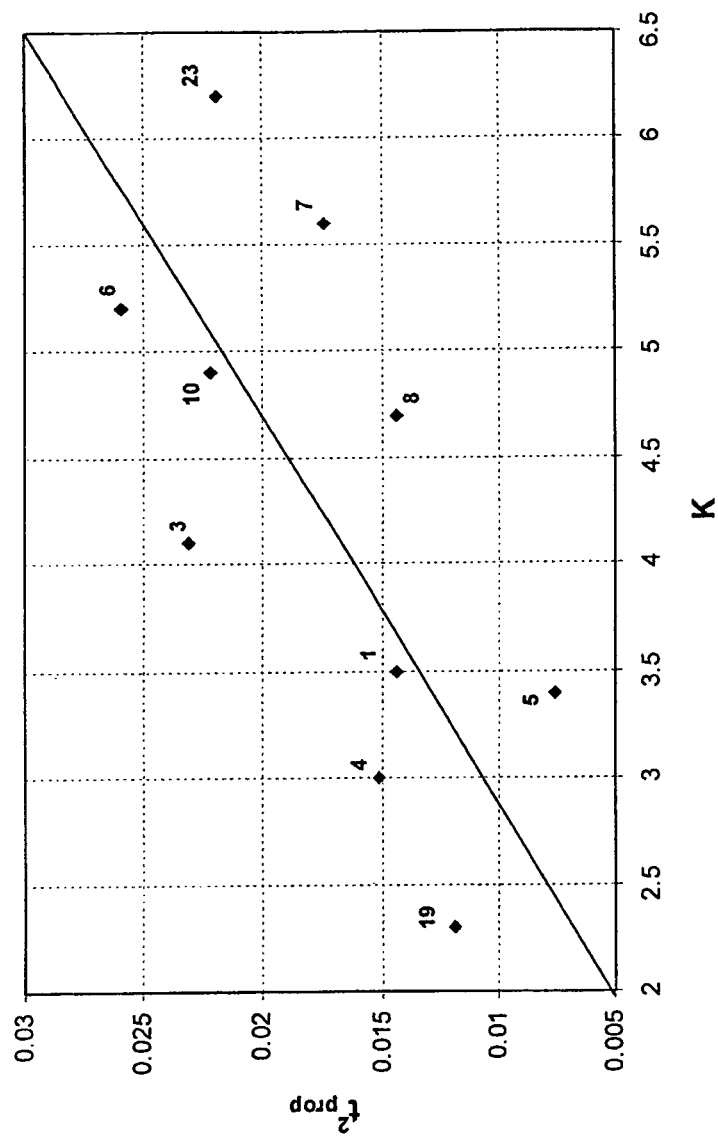
FIG. 4 is a graph illustrating the relationship between the pulse pressure propagation time and vascular tone on patients recovering from cardiac arrest according to an embodiment of the invention.

FIG. 4 is a graph illustrating the relationship between the square of the arterial pulse pressure propagation time and the scaling factor K of patients during recovery from cardiac bypass surgery. FIG. 4 plots ten (10) averaged data points from ten (10) different patients. In the example of FIG. 4, the arterial pulse pressure propagation time has been calculated as a transit time between the ECG signal and the radial arterial pressure. The data shown in FIG. 4 illustrates that the K scaling factors of equation 17 can be effectively estimated using the arterial pulse pressure propagation time as given by equation 16.

Figure 5:
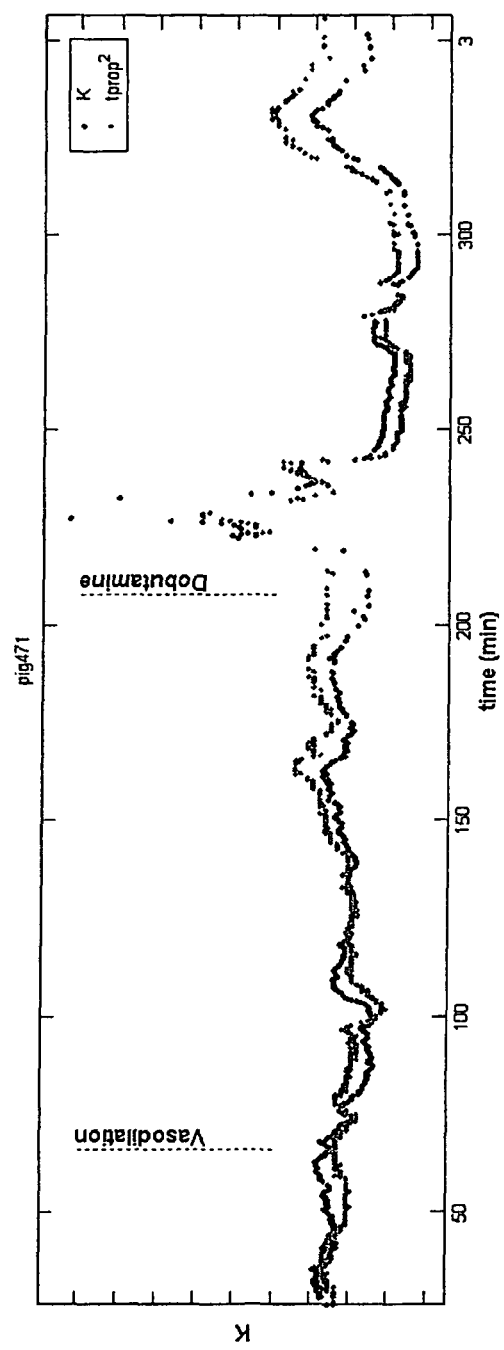
FIGS. 5-6 are graphs illustrating the correlation between the pulse pressure propagation time and vascular tone for different hemodynamic conditions of the subjects according to several embodiments of the invention.
Figure 6:
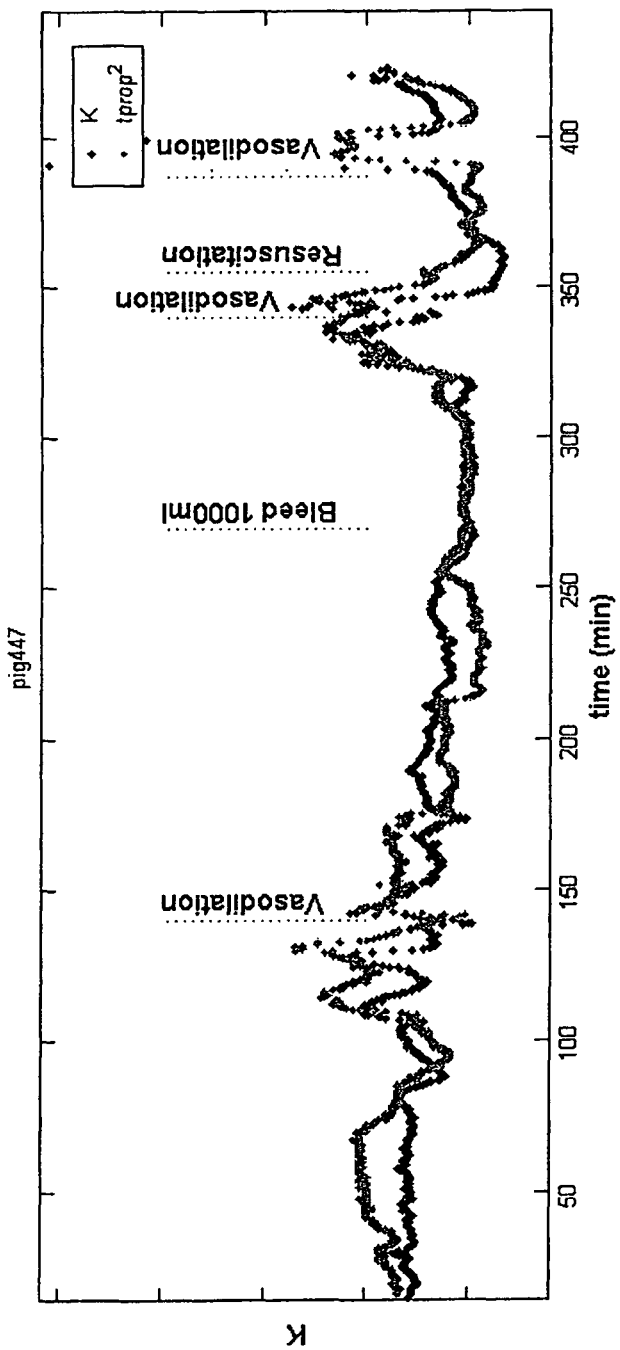

FIGS. 5 and 6 are graphs illustrating the correlation between the arterial pulse pressure propagation time and the K scaling factor of equation 17 for different hemodynamic states of two subjects. Both trends correspond to animal data taken from experiments using porcine animal models. These figures show identical trends of the scaling factor K and the square of the pulse pressure propagation time. The data on FIGS. 5 and 6 illustrate that the K or the C scaling factors of equations 17 and 18 can be effectively estimated using the arterial pulse pressure propagation time.

The scaling factor γ of equation 19 can be determined using any pre-determined function of the propagation time and the pressure P(t); thus, $$\gamma = \Gamma(t_{prop}, P) \quad \text{(Equation 22)}$$

where Γ is a pre-determined function of the propagation time and pressure, used to develop computational methods to estimate γ.

Any known, independent CO technique may be used to determine this relationship, whether invasive, for example, thermodilution, or non-invasive, for example, trans-esophageal echocardiography (TEE) or bio-impedance measurement. The invention provides continuous trending of CO between intermittent measurements such as TD or TEE.

Even if an invasive technique such as catheterization is used to determine γ, it will usually not be necessary to leave the catheter in the patient during the subsequent CO-monitoring session. Moreover, even when using a catheter-based calibration technique to determine γ, it is not necessary for the measurement to be taken in or near the heart; rather, the calibration measurement can be made in the femoral artery. As such, even where an invasive technique is used to determine γ, the invention as a whole is still minimally invasive in that any catheterization may be peripheral and temporary.

As discussed above, rather than measure arterial blood pressure directly, any other input signal may be used that is proportional to blood pressure. This means that calibration may be done at any or all of several points in the calculations. For example, if some signal other than arterial blood pressure itself is used as an input signal, then it may be calibrated to blood pressure before its values are used to calculate standard deviation, or afterwards, in which case either the resulting standard deviation value can be scaled, or the resulting SV value can be calibrated (for example, by setting γ properly), or some final function of SV (such as CO) can be scaled. In short, the fact that the invention may in some cases use a different input signal than a direct measurement of arterial blood pressure does not limit its ability to generate an accurate SV estimate.

In addition to the blood viscosity, γ depends mainly of the physical vascular volume between the two recording sites. Of course, the effective length (L) and the effective volume (V) between the two recording sites can not be known. Vascular branching and the patient to patient differences are two main reasons why the effective physical vascular volume between the two recording sites can not be known. However, it is obvious that this physical volume is proportional to the patient's anthropometric parameters and therefore it can be estimated indirectly using the patient's anthropometric parameters. The anthropometric parameters may be derived from various parameters such as the measured distance (l) between the two recording sites, patient's weight, patient's height, patient's gender, patient's age, patient's bsa, etc., or any combination of these factors. In one embodiment, all the anthropometric parameters, for example, the distance (l) between the two recording sites, patient's weight, patient's height, patient's gender, patient's age and patient's bsa, may be used to compute γ. Additional values are preferably also included in the computation to take other characteristics into account. In one embodiment, the heart rate HR (or period of R-waves) may be used. Thus, $$\gamma = \Gamma_M(l, H, W, BSA, Age, G, HR) \quad \text{(Equation 23)}$$

Where
l is the measured distance between the two recording sites;
H is the patient's height;
W is the patient's weight;
BSA is the patient's bsa;
Age is the patient's age;
G is the patient's gender;
HR is the patient's heart rate; and
ΓM is a multivariate model.

The predictor variables set for computing γ, using the multivariate model Γ, are related to the "true" vascular compliance measurement, determined as a function of CO measured through thermo-dilution and the arterial pulse pressure, for a population of test or reference subjects. This creates a suite of compliance measurements, each of which is a function of the component parameters of $\Gamma_M$. The multivariate approximating function is then computed using numerical methods that best relates the parameters of $\Gamma_M$ to a given suite of CO measurements in a predefined manner. A polynomial multivariate fitting function is used to generate the coefficients of the polynomial that give a value of $\Gamma_M$ for each set of the predictor variables. Thus, the multivariate model has the following general equation:

$$\Gamma_M = [a_1 \; a_2 \; \cdots \; a_n] * \begin{bmatrix} Y_1 \\ Y_2 \\ \vdots \\ Y_n \end{bmatrix} \quad \text{(Equation 24)}$$

where $a_1 \ldots a_n$ are the coefficients of the polynomial multiregression model, and Y are the model's predictor variables:

$$Y_{n,1} = \quad \text{(Equation 25)}$$

$$\prod_m \left( [l \; H \; W \; BSA \; Age \; G \; HR] \begin{bmatrix} P_{1,1} & \cdots & P_{1,m} \\ \cdots & \cdots & \cdots \\ P_{n,1} & \cdots & P_{n,m} \end{bmatrix} \right)$$

The use of the arterial pulse pressure propagation time to estimate vascular tone. Vascular tone is a hemodynamic parameter used to describe the combined effect of vascular compliance and peripheral resistance. In the prior art, the shape characteristics of the arterial pressure waveform in combination with patients anthropometric data and other cardiovascular parameters were used to estimate vascular tone (see Roteliuk, 2005, "Arterial pressure-based automatic determination of a cardiovascular parameter"). The arterial pulse pressure propagation time can also be used to estimate vascular tone. In one embodiment, the arterial pulse pressure propagation time can be used as an independent term to a multivariate regression model to continuously estimate vascular tone. In one embodiment, the arterial pulse pressure propagation time can be used in combination with the shape information of the arterial pulse pressure waveform to estimate the vascular tone. The higher order shape sensitive arterial pressure statistical moments and the pressure-weighted time moments may be used as predictor variables in the multivariate model along with the arterial pulse pressure propagation time. Additional values are preferably also included in the computation to take other characteristics into account. For example, the heart rate HR (or period of R-waves), the body surface area BSA, as well as a pressure dependent non-linear compliance value C(P) may be calculated using a known method such as described by Langwouters, which computes compliance as a polynomial function of the pressure waveform and the patient's age and sex. Thus, $$K = \chi(t_{prop}, \mu_{T1}, \mu_{T2}, \ldots \mu_{Tk}, \mu_{P1}, \mu_{P2}, \ldots \mu_{Pk}, C(P), BSA, Age, G \ldots) \quad \text{(Equation 26)}$$

where
K is vascular tone;
X is a multiregression statistical model;
$t_{prop}$ is the arterial pulse pressure propagation time;
$\mu_{1T} \ldots \mu_{kT}$ are the 1-st to k-th order time domain statistical moments of the arterial pulse pressure waveform;
$\mu_{1P} \ldots \mu_{kP}$ are the lest to k-th order pressure weighted statistical moments of the arterial pulse pressure waveform;
C(P) is the pressure dependent vascular compliance as defined by Langwouters et al. ("The Static Elastic Properties of 45 Human Thoracic and 20 Abdominal Aortas in vitro and the Parameters of a New Model," J. Biomechanics, Vol. 17, No. 6, pp. 425-435, 1984);
BSA is the patient's body surface area (function of height and weight);
Age is the patient's age; and
Gender is the patient's gender.

Depending on the needs of a given implementation of the invention, one may choose not to include either skewness or kurtosis, or one may include even higher order moments. The use of the first four statistical moments has proven successful in contributing to an accurate and robust estimate of compliance. Moreover, anthropometric parameters other than the HR and BSA may be used in addition, or instead, and other methods may be used to determine C(P), which may even be completely omitted.

The exemplary method described below for computing a current vascular tone value may be adjusted in a known manner to reflect the increased, decreased, or altered parameter set. Once the parameter set for computing K has been assembled, it may be related to a known variable. Existing devices and methods, including invasive techniques, such as thermo-dilution, may be used to determine CO, HR and $SV_{est}$ for a population of test or reference subjects. For each subject, anthropometric data such as age, weight, BSA, height, etc. can also be recorded. This creates a suite of CO measurements, each of which is a function (initially unknown) of the component parameters of K. An approximating function can therefore be computed, using known numerical methods, that best relates the parameters to K given the suite of CO measurements in some predefined sense. One well understood and easily computed approximating function is a polynomial. In one embodiment, a standard multivariate fitting routine is used to generate the coefficients of a polynomial that gave a value of K for each set of parameters $t_{prop}$, HR, C(P), BSA, $\mu_{1P}, \sigma_P, \mu_{3P}, \mu_{4P}, \mu_{1T}, \sigma_T, \mu_{3T}, \mu_{4T}$.

In one embodiment, K is computed as follows:

$$K = [A_1 \quad A_2 \quad \cdots \quad A_n] * \begin{bmatrix} X_1 \\ X_2 \\ \cdots \\ X_n \end{bmatrix} \quad \text{(Equation 27)}$$

where $$X_{n,1} = \prod_m \left( \left[ t_{prop}, \mu_{T1}, \mu_{T2}, \ldots \mu_{T2}, \mu_{P1}, \mu_{P2}, \ldots \atop \mu_{Pk}, C(P), BSA, Age, G\ldots \right] \wedge \begin{bmatrix} P_{1,1} & \cdots & P_{1,m} \\ \cdots & \cdots & \cdots \\ P_{n,1} & \cdots & P_{n,m} \end{bmatrix} \right) \quad \text{(Equation 28)}$$

3. The use of the arterial pulse pressure propagation to directly estimate CO is discussed below.

The pulse pressure propagation time may be used as an independent method to estimate CO. That is, the arterial pulse pressure propagation time is independently proportional to SV, as shown below:

$$SV = K_p \cdot \frac{1}{t_{prop}} \quad \text{(Equation 29)}$$

CO can be estimated if we multiply equation 29 by HR:

$$\boxed{CO = K_p \cdot \frac{1}{t_{prop}} \cdot HR} \quad \text{(Equation 30)}$$

Figure 7:
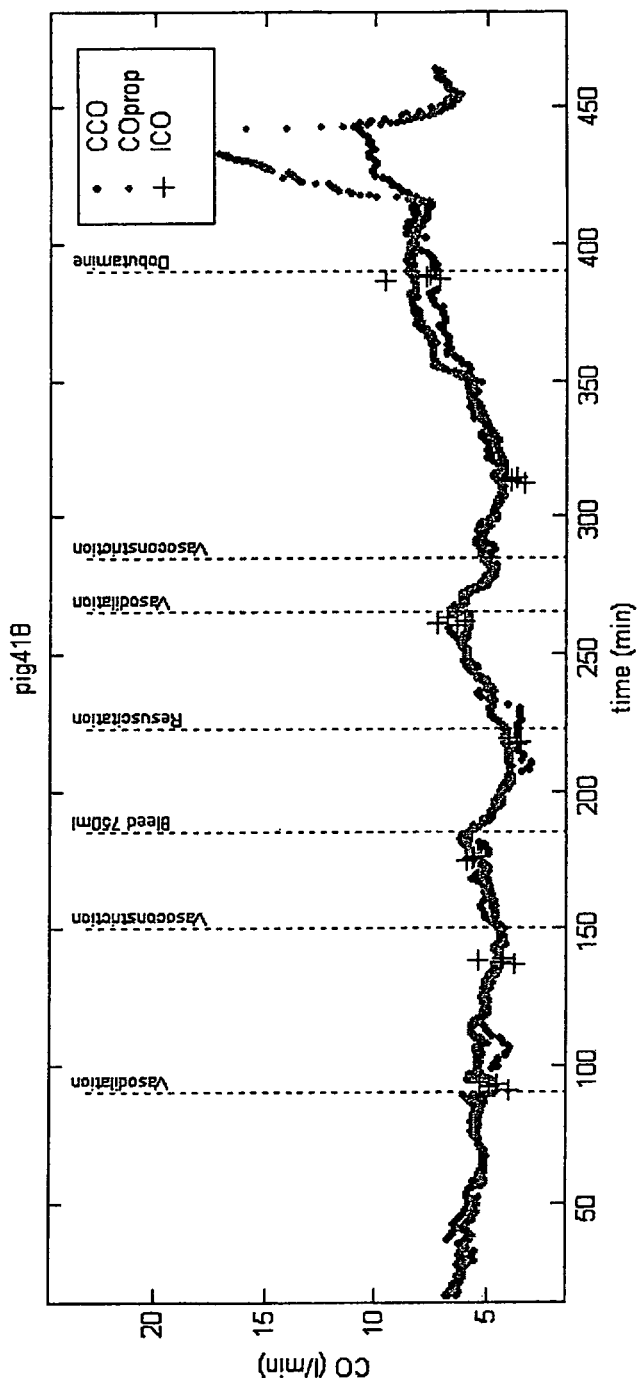
FIGS. 7-9 are graphs illustrating the correlation between the CO computed using the pulse pressure propagation time, Continuous Cardiac Output (CCO) and CO values measured by thermodilution bolus measurements (TD-CO) for different hemodynamic states of the subjects according to several embodiments of the invention.
Figure 8:
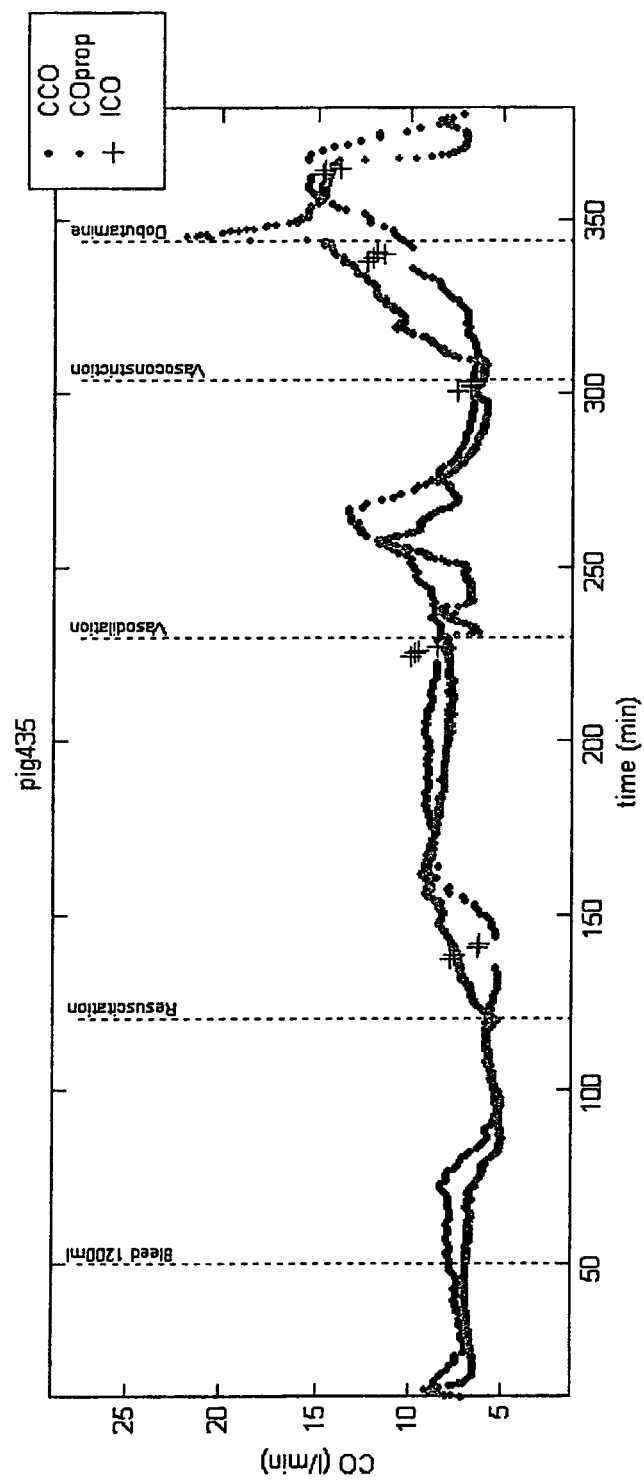
Figure 9:
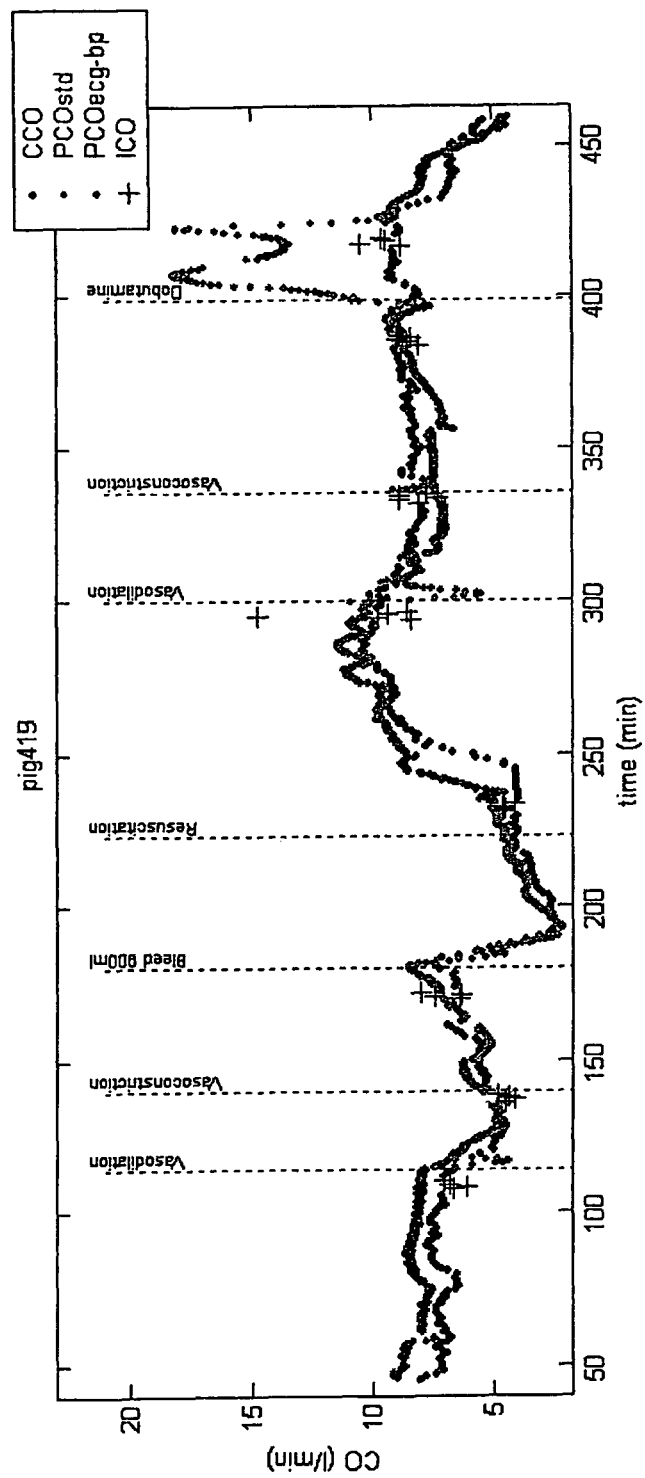

The scaling factor $K_p$ can be estimated using a direct calibration, for example, using a known CO value from a bolus thermo-dilution measurement or other gold standard CO measurement. FIGS. 7-9 are graphs illustrating the correlation between the CO computed using the pulse pressure propagation time as shown in equation 30 (COprop), Continuous Cardiac Output (CCO) and CO values measured by intermittent thermodilution bolus measurements (ICO). CCO and ICO are measured using the Vigilance monitor manufactured by Edwards Lifesciences of Irvine, Calif. The measurements have been performed on animal porcine models in different hemodynamic states of the animals. These graphs show experimentally that changes in CO are related to changes in the pulse pressure propagation time and that the pulse pressure propagation time can be used as an independent method to estimate CO.

The scaling factor $K_p$ of equation 30 can be determined using any pre-determined function of the propagation time and CO or SV. Any independent CO technique may be used to determine this relationship, whether invasive, for example, thermo-dilution, or non-invasive, for example, trans-esophageal echocardiography (TEE) or bio-impedance measurement. The invention provides continuous trending of CO between intermittent measurements such as TD or TEE.

Even if an invasive technique such as catheterization is used to determine $K_p$, it may not be necessary to leave the catheter in the patient during the subsequent CO-monitoring session. Moreover, even when using catheter-based calibration technique to determine $K_p$, it may not be necessary for the measurement to be taken in or near the heart; rather, the calibration measurement can be made in the femoral artery. As such, even where an invasive technique is used to determine $K_p$, the method is still minimally invasive in that any catheterization may be peripheral and temporary.

The approach shown in equation 30 allows measuring CO to be performed completely non-invasively if non-invasive techniques are used to measure the propagation time and if a predefined function or relationship is used to measure $K_p$. The non-invasive techniques to measure the propagation time can include, but are not limited to: ECG, non-invasive arterial blood pressure measurements, bio-impedance measurements, optical pulse oximetry measurements, Doppler ultrasound measurements, or any other measurements derived from or proportional to them or any combination of them (for example: using Doppler ultrasound pulse velocity measurement to measure the reference signal near the heart and using a bio-impedance measurement to measure the peripheral signal . . . etc).

The scaling factor $K_p$, depends mainly on blood viscosity and the physical vascular distance and volume between the two recording sites. Of course, the effective length (L) and the effective volume (V) between the two recording sites can not be known. Vascular branching and the patient to patient differences are two main reasons why the effective physical vascular volume between the two recording sites can not be known. However, the physical volume may be proportional to the patient's anthropometric parameters and therefore it can be estimated indirectly using the patient's anthropometric parameters. The anthropometric parameters may be derived from various parameters such as the measured distance (L) between the two recording sites, patient's weight, patient's height, patient's gender, patient's age, patient's bsa etc., or any combination of these parameters. In one embodiment, all the anthropometric parameters: the distance (L) between the two recording sites, patient's weight, patient's height, patient's gender, patient's age and patient's bsa are used to compute $K_p$. Thus, $$K_p = M(L,H,W,BSA,Age,G) \quad \text{(Equation 31)}$$

where
L is the measured distance between the two recording sites;
H is the patient's height;
W is the patient's weight;
BSA is the patient's bsa;
Age is the patient's age;
G is the patient's gender; and
M is a multivariate linear regression model.

The predictor variables set for computing $K_p$, using the multivariate model M, are related to the "true" CO measurement, determined as a function of the propagation time, where CO is measured through thermo-dilution, for a population of test or reference subjects. This creates a suite of measurements, each of which is a function of the component parameters of M. The multivariate approximating function is then computed using numerical methods that best relates the parameters of M to a given suite of CO measurements in some predefined sense. A polynomial multivariate fitting function is used to generate the coefficients of the polynomial that give a value of M for each set of the predictor variables. Thus, the multivariate model has the following equation:

$$M = [a_1 \quad a_2 \quad \cdots \quad a_n] * \begin{bmatrix} Y_1 \\ Y_2 \\ \cdots \\ Y_n \end{bmatrix} \quad \text{(Equation 32)}$$

where $a_1 \ldots a_n$ are the coefficients of the polynomial multiregression model, and Y are the model's predictor variables:

$$Y_{n,1} = \prod_m \left( [L \ H \ W \ BSA \ Age \ G] \wedge \begin{bmatrix} p_{1,1} & \cdots & p_{1,m} \\ \cdots & \cdots & \cdots \\ p_{n,1} & \cdots & p_{n,m} \end{bmatrix} \right) \quad \text{(Equation 33)}$$

Figure 10:
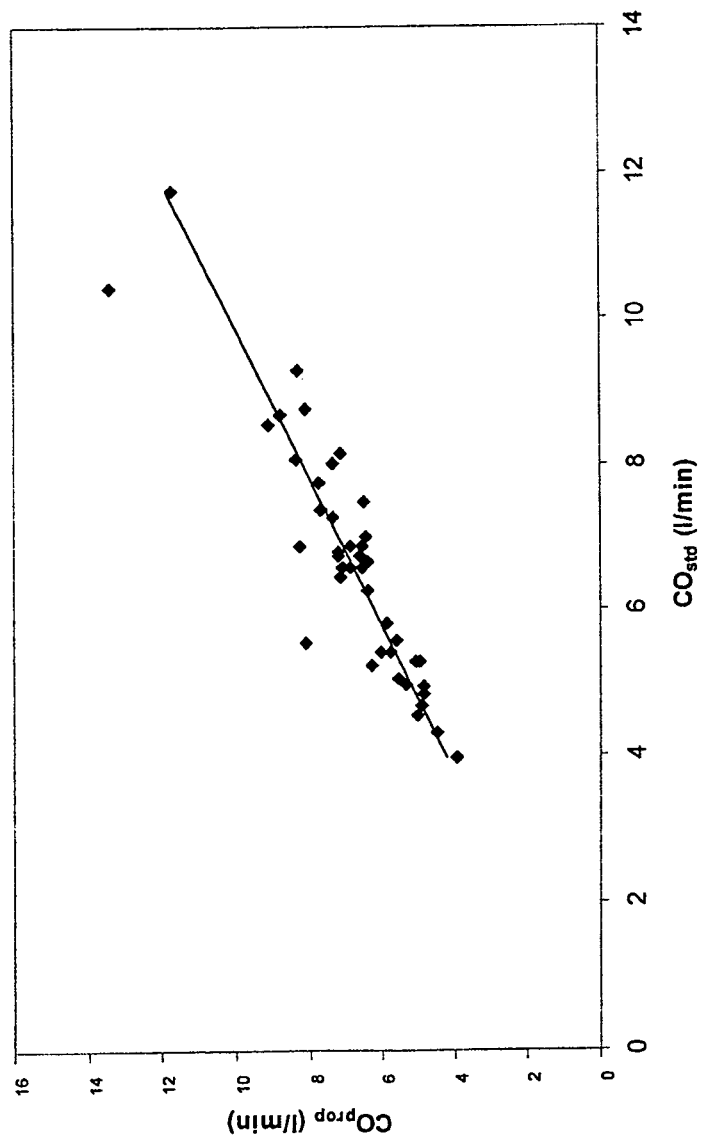
FIG. 10 is a graph showing the relationship between the CO estimated using the arterial pressure propagation time according to several embodiments of the invention and CO estimated using the arterial pulse pressure signal.

FIG. 10 is a graph showing the relationship between the CO estimated using equation 17 ($CO_{std}$ on the x-axis) and CO estimated using equation 30 ($CO_{prop}$ on the y-axis) from a series of animal experiments. The data shows CO measurements from a total of ten (10) pigs. Three (3) selected data points from each pig are used for the graph. In order to cover a wide CO range, each selected data point corresponds to a different hemodynamic state of the pig: vasodilated, vasoconstricted and hypovolemic states, respectively. The proportionality shown in FIG. 10 is experimental proof of the effectiveness and the reliability of using the propagation time to estimate CO.

Figure 11:
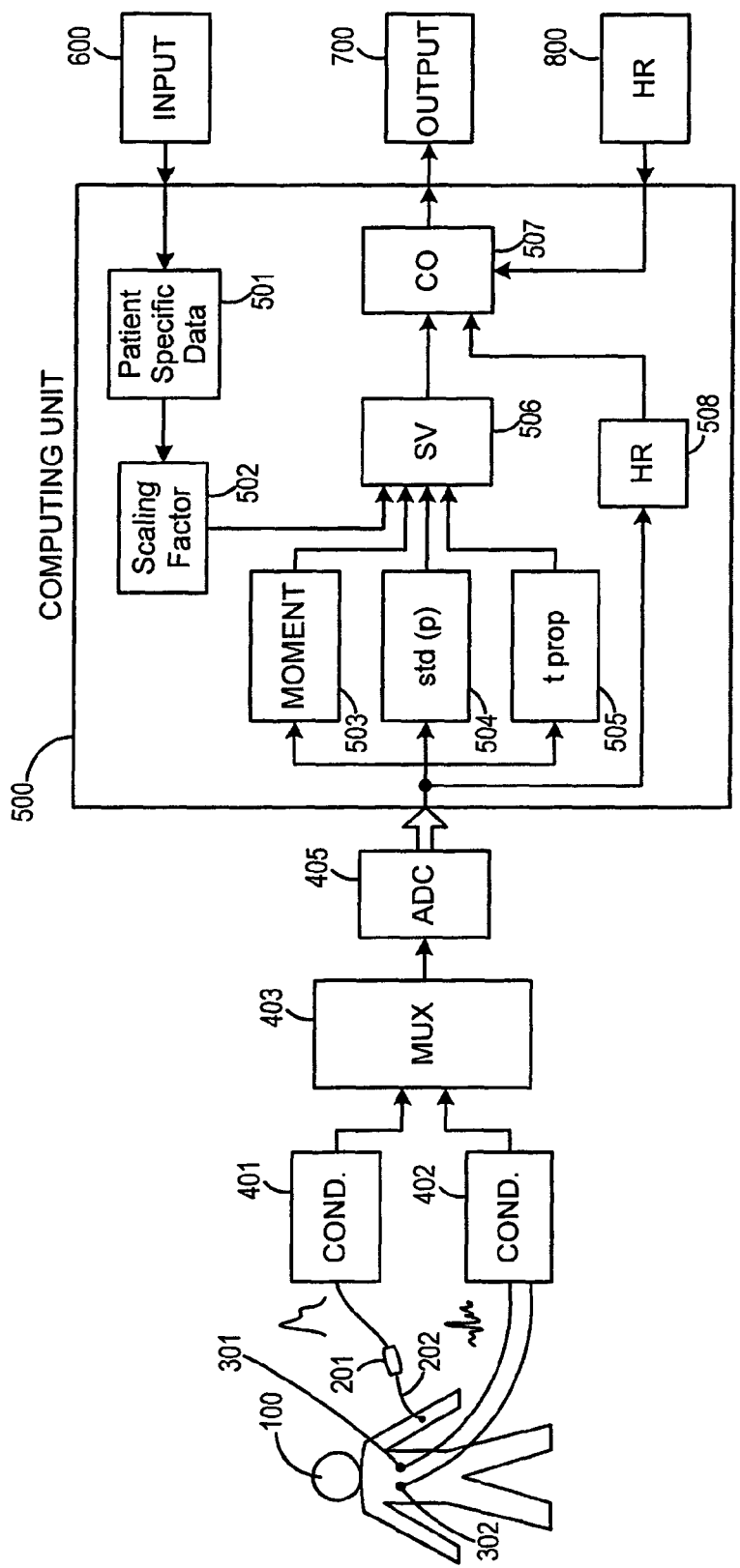
FIG. 11 is a block diagram showing an exemplary system used to execute the various methods described herein according to several embodiments of the invention.
Figure 12:
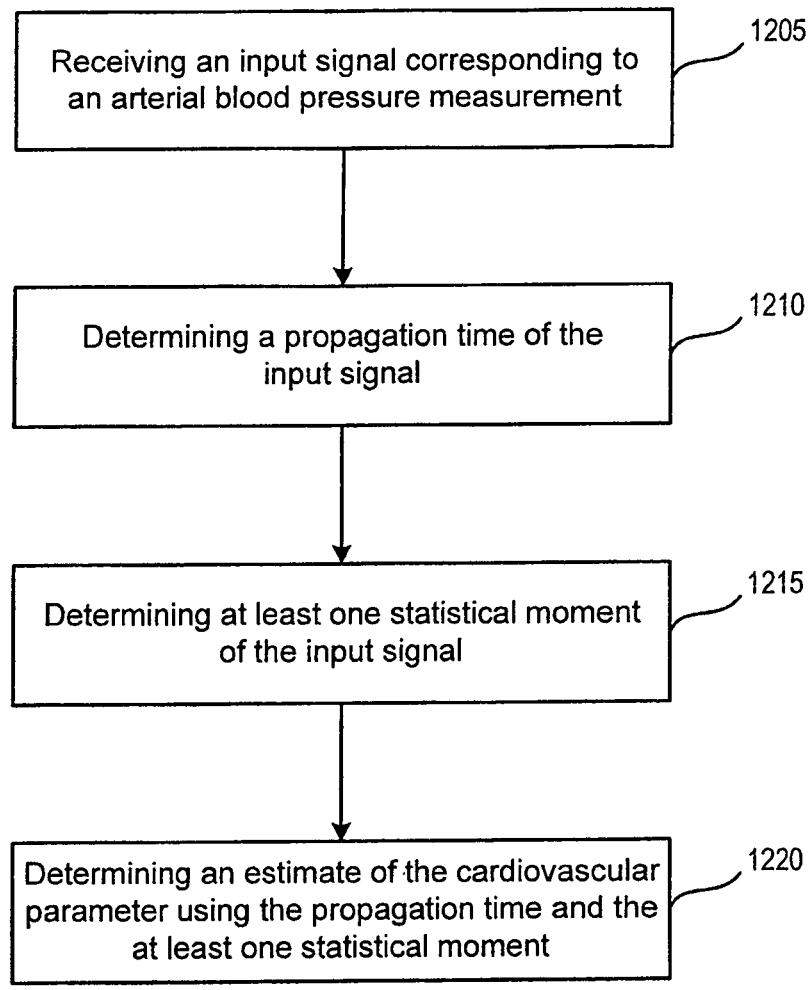
FIG. 12 is a flow chart showing a method according to an embodiment of the invention.

FIG. 11 is a block diagram showing an exemplary system used to execute the various methods described herein. The system may include a patient 100, a pressure transducer 201, a catheter 202, ECG electrodes 301 and 302, signal conditioning units 401 and 402, a multiplexer 403, an analog-to-digital converter 405 and a computing unit 500. The computing unit 500 may include a patient specific data module 501, a scaling factor module 502, a moment module 503, a standard deviation module 504, a propagation time module 505, a stroke volume module 506, a cardiac output module 507, a heart rate module 508, an input device 600, an output device 700, and a heart rate monitor 800. Each unit and module may be implemented in hardware, software, or a combination of hardware and software.

The patient specific data module 501 is a memory module that stores patient data such as a patient's age, height, weight, gender, BSA, etc. This data may be entered using the input device 600. The scaling factor module 502 receives the patient data and performs calculations to compute the scaling compliance factor. For example, the scaling factor module 502 puts the parameters into the expression given above or into some other expression derived by creating an approximating function that best fits a set of test data. The scaling factor module 502 may also determine the time window [t0, tf] over which each vascular compliance, vascular tone, SV and/or CO estimate is generated. This may be done as simply as choosing which and how many of the stored, consecutive, discretized values are used in each calculation.

The moment module 503 determines or estimates the arterial pulse pressure higher order statistical time domain and weighted moments. The standard deviation module 504 determines or estimates the standard deviation of the arterial pulse pressure waveform. The propagation time module 505 determines or estimates the propagation time of the arterial pulse pressure waveform.

The scaling factor, the higher order statistical moments, the standard deviation and the propagation time are input into the stroke volume module 506 to produce a SV value or estimate. A heart rate monitor 800 or software routine 508 (for example, using Fourier or derivative analysis) can be used to measure the patient's heart rate. The SV value or estimate and the patient's heart rate are input into the cardiac output module 507 to produce an estimate of CO using, for example, the equation CO=SV*HR.

As mentioned above, it may not be necessary for the system to compute SV or CO if these values are not of interest. The same is true for the vascular compliance, vascular tone and peripheral resistance. In such cases, the corresponding modules may not be necessary and may be omitted. For example, the invention may be used to determined arterial compliance. Nonetheless, as FIG. 11 illustrates, any or all of the results, SV, CO, vascular compliance, vascular tone and peripheral resistance may be displayed on the output device 700 (e.g., a monitor) for presentation to and interpretation by a user. As with the input device 600, the output device 700 may typically be the same as is used by the system for other purposes.

The invention further relates to a computer program loadable in a computer unit or the computing unit 500 in order to execute the method of the invention. Moreover, the various modules 501-507 may be used to perform the various calculations and perform related method steps according to the invention and may also be stored as computer-executable instructions on a computer-readable medium in order to allow the invention to be loaded into and executed by different processing systems.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described preferred embodiment can be configured without departing from the scope and spirit of the invention. Therefore, it is to be understood that, within the scope of the appended claims, the invention may be practiced other than as specifically described herein.

What is claimed is:

1. A method for determining a cardiovascular parameter comprising:
   receiving an input signal corresponding to an arterial blood pressure measurement over an interval that covers at least one cardiac cycle;
   determining a propagation time of the input signal;
   determining at least one statistical moment of the input signal; and
   determining, using at least a portion of a computing unit, an estimate of the cardiovascular parameter using the propagation time and the at least one statistical moment, wherein the cardiovascular parameter is selected from a group consisting of cardiac output and stroke volume.

2. The method as defined in claim 1 wherein the at least one statistical moment of the input signal is selected from a group consisting of a standard deviation of the input signal, kurtosis of the input signal and skewness of the input signal.

3. The method as defined in claim 1 wherein the step of determining a propagation time of the input signal includes determining a transit time between a reference signal detected near a heart of a subject and a peripheral arterial signal detected near an artery of the subject.

4. The method as defined in claim 3 wherein the reference signal is selected from a group consisting of an electrocardiogram measurement, a central aortic pressure measurement, a transthoracic bioimpedance measurement and a Doppler ultrasound blood velocity measurement.

5. The method as defined in claim 3 wherein the peripheral arterial signal is selected from a group consisting of an arterial blood pressure measurement, an optical oximetry measurement that measures the oxygen saturation of the blood of the subject, a peripheral bioimpedance measurement and a Doppler ultrasound blood velocity measurement.

6. The method as defined in claim 1 wherein determining an estimate of the cardiovascular parameter using the propagation time includes using a standard deviation of the input signal to determine an estimate of the cardiovascular parameter.

7. The method as defined in claim 1 further comprising receiving an anthropometric parameter of the subject.

8. The method as defined in claim 7 wherein determining an estimate of the cardiovascular parameter using the propagation time also includes using the anthropometric parameter to determine an estimate of the cardiovascular parameter.

9. The method as defined in claim 7 further comprising estimating an arterial compliance value using the propagation time and the anthropometric parameter.

10. The method as defined in claim 9 further comprising estimating a stroke volume using the arterial compliance value and a standard deviation of the input signal.

11. The method as defined in claim 10 further comprising:
receiving a heart rate measurement of a subject; and
estimating cardiac output using the heart rate measurement and the stroke volume.

12. The method as defined in claim 9 further comprising generating a cardiac output estimate using the arterial compliance and the standard deviation.

13. The method as defined in claim 12 further comprising:
receiving a calibration cardiac output value; and
calculating a calibration constant as a quotient between the calibration cardiac output estimate and the product of the heart rate, the arterial compliance and the standard deviation.

14. The method as defined in claim 9 wherein estimating an arterial compliance value further comprises:
determining an approximating function relating to a plurality of reference measurements to arterial compliance, wherein the approximating function is a function of the propagation time of the input signal and the anthropometric parameter; and
estimating the arterial compliance value of the subject by evaluating the approximating function with the propagation time of the input signal and the anthropometric parameter.

15. The method as defined in claim 1 further comprising:
calculating a component propagation time value for each cardiac cycle from amongst a plurality of cardiac cycles;
computing a composite propagation time value as an average of the component propagation time values; and
using the composite propagation time value in calculating an estimate of the cardiovascular parameter.

* * * * *